United States Patent
Suzuki

(10) Patent No.: US 9,687,146 B2
(45) Date of Patent: Jun. 27, 2017

(54) ADAPTIVE OPTICAL APPARATUS, IMAGING APPARATUS, AND CONTROL METHOD AND PROGRAM

(71) Applicant: CANON KABUSHIKI KAISHA, Tokyo (JP)

(72) Inventor: Kei Suzuki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 367 days.

(21) Appl. No.: 14/087,294

(22) Filed: Nov. 22, 2013

(65) Prior Publication Data

US 2014/0146286 A1    May 29, 2014

(30) Foreign Application Priority Data

Nov. 29, 2012    (JP) .................................. 2012-261633

(51) Int. Cl.
| | | |
|---|---|---|
| *A61B 3/10* | (2006.01) | |
| *A61B 3/117* | (2006.01) | |
| *A61B 3/14* | (2006.01) | |

(52) U.S. Cl.
CPC ............ *A61B 3/1015* (2013.01); *A61B 3/117* (2013.01); *A61B 3/14* (2013.01)

(58) Field of Classification Search
CPC ..... A61B 3/1015; A61B 3/117; A61B 3/0008; A61B 3/0025; A61B 3/0075; A61B 3/10; A61B 3/113; A61B 3/14
See application file for complete search history.

(56) References Cited

U.S. PATENT DOCUMENTS

| | | | | |
|---|---|---|---|---|
| 4,149,787 A | * | 4/1979 | Kobayashi ............... | A61B 3/14 351/206 |
| 4,486,080 A | * | 12/1984 | Itoh ......................... | A61B 3/10 351/206 |
| 4,762,410 A | * | 8/1988 | Sekiguchi ................ | A61B 3/11 351/206 |
| 5,486,892 A | | 1/1996 | Suzuki et al. | |
| 5,907,722 A | | 5/1999 | Suzuki | |
| 6,014,524 A | | 1/2000 | Suzuki et al. | |
| 2007/0229760 A1 | | 10/2007 | Hirohara et al. | |
| 2007/0252951 A1 | | 11/2007 | Hammer et al. | |
| 2007/0258095 A1 | | 11/2007 | Olivier et al. | |
| 2009/0115968 A1 | * | 5/2009 | Sugiyama ............ | G02B 27/017 351/221 |

(Continued)

FOREIGN PATENT DOCUMENTS

| | | |
|---|---|---|
| JP | 2009-112665 A | 5/2009 |
| JP | 2011-104125 A | 6/2011 |

OTHER PUBLICATIONS

Mar. 27, 2014 European Search Report in European Patent Appln. No. 13192022.5.

*Primary Examiner* — Jordan Schwartz
(74) *Attorney, Agent, or Firm* — Fitzpatrick, Cella, Harper & Scinto

(57) ABSTRACT

An adaptive optical apparatus includes: a correction unit configured to correct a wavefront aberration of an eye to be examined; a detection unit configured to detect that an eyelid of the eye to be examined is closed or the eyelid of the eye to be examined is open, by using return light from the eye to be examined irradiated by measurement light; and a control unit configured to control the correction unit according to a detection result from the detection unit.

22 Claims, 5 Drawing Sheets

(56) References Cited

U.S. PATENT DOCUMENTS

| | | | |
|---|---|---|---|
| 2011/0116042 A1* | 5/2011 | Nozato | A61B 3/1015 351/206 |
| 2011/0152845 A1 | 6/2011 | Hammer et al. | |
| 2013/0100405 A1 | 4/2013 | Porter et al. | |
| 2014/0118697 A1* | 5/2014 | Tanaka | A61B 3/14 351/208 |

* cited by examiner

F I G. 2
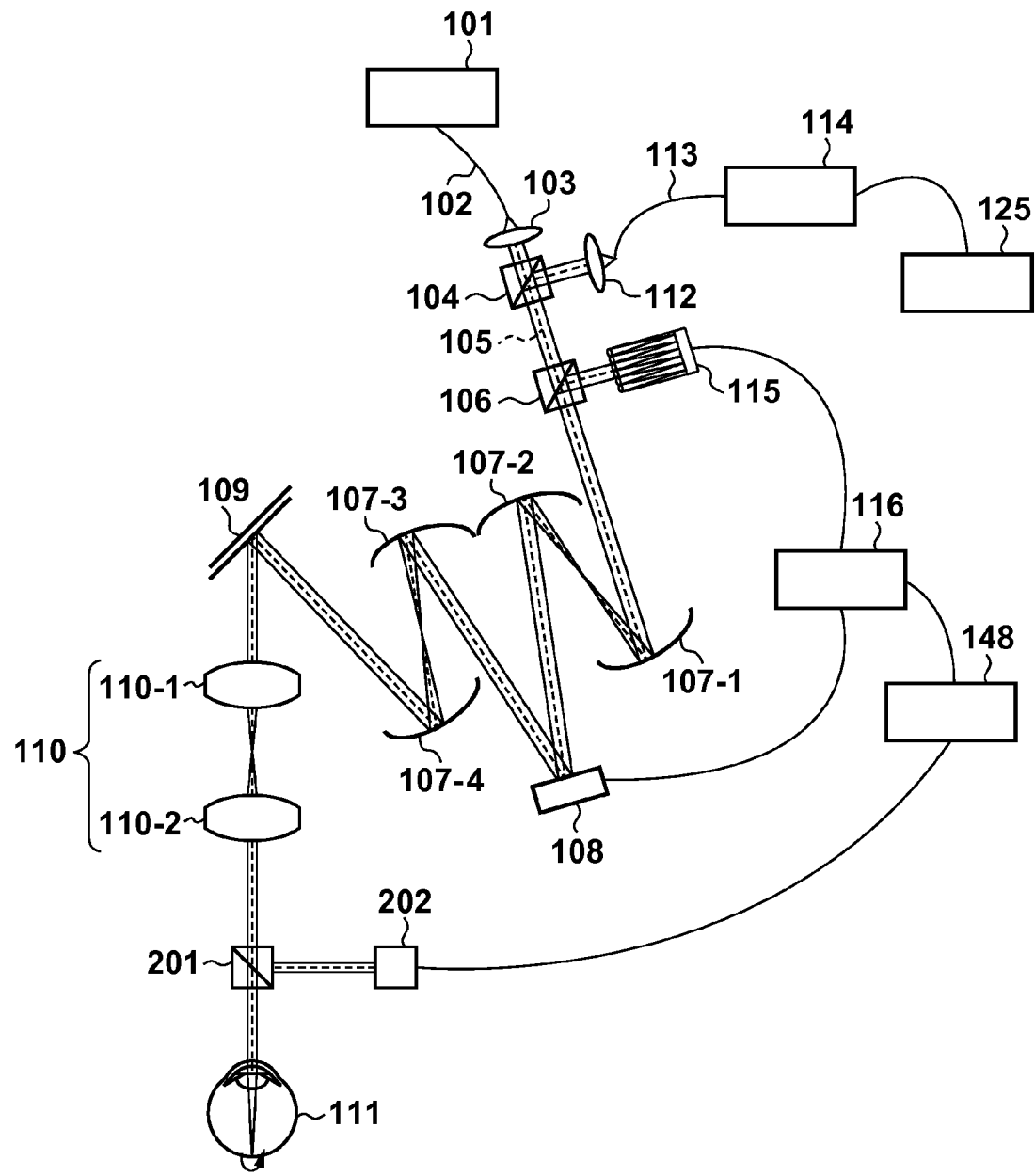

F I G. 3A
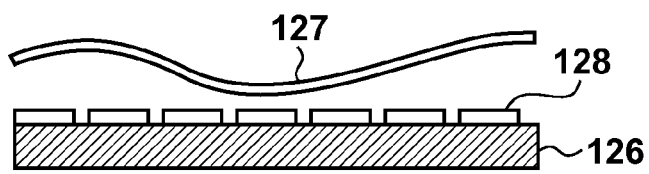
F I G. 3B
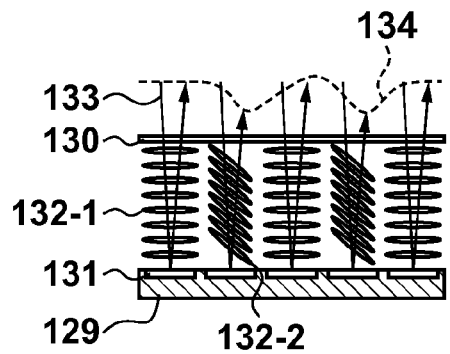
F I G. 3C-1
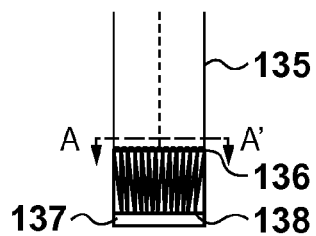
F I G. 3C-2
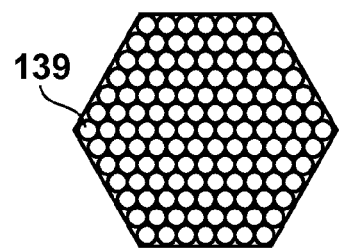
F I G. 3D
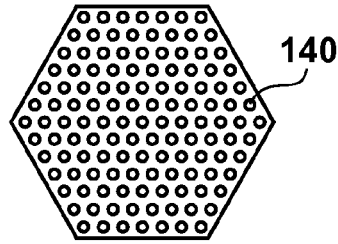
F I G. 3E-1
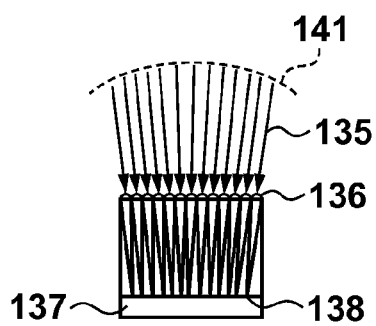
F I G. 3E-2
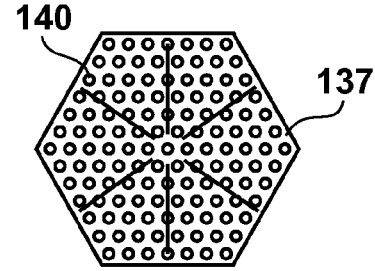

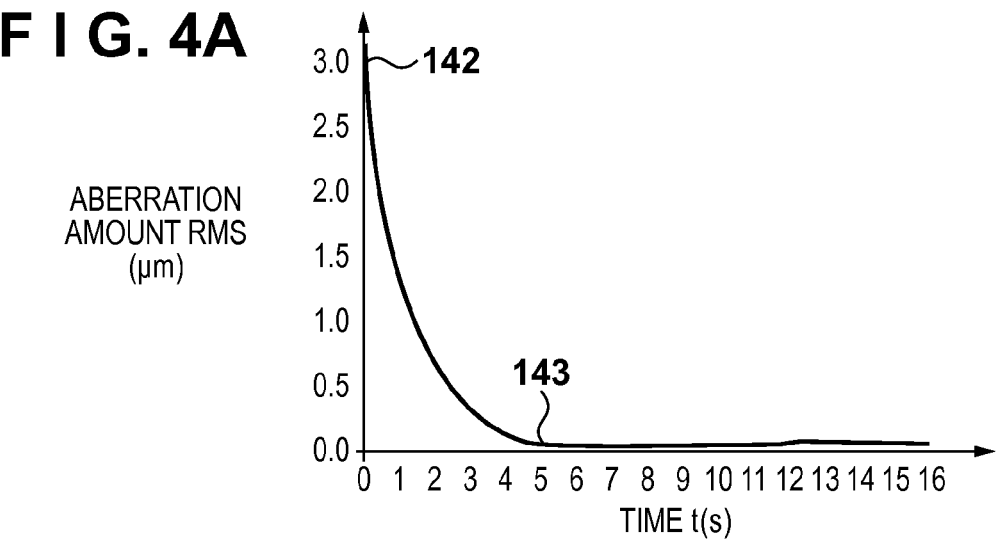
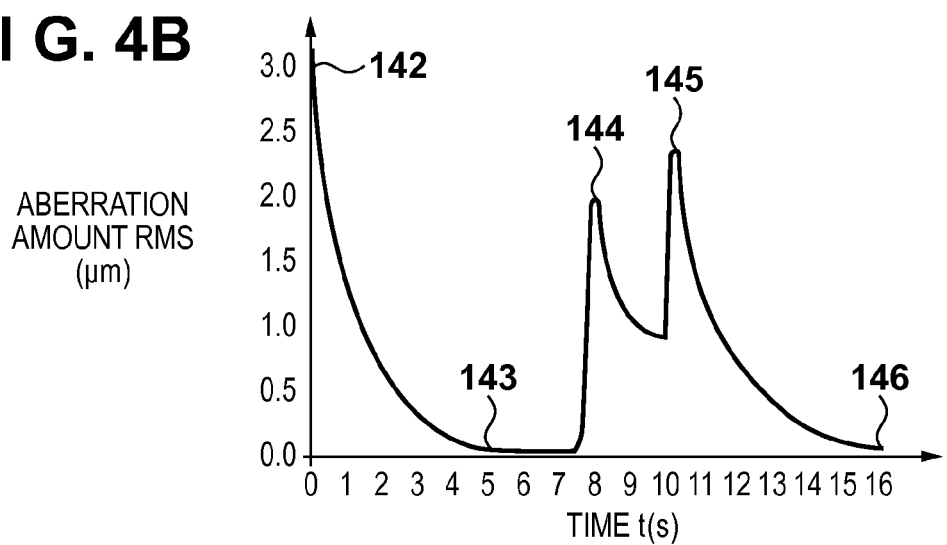
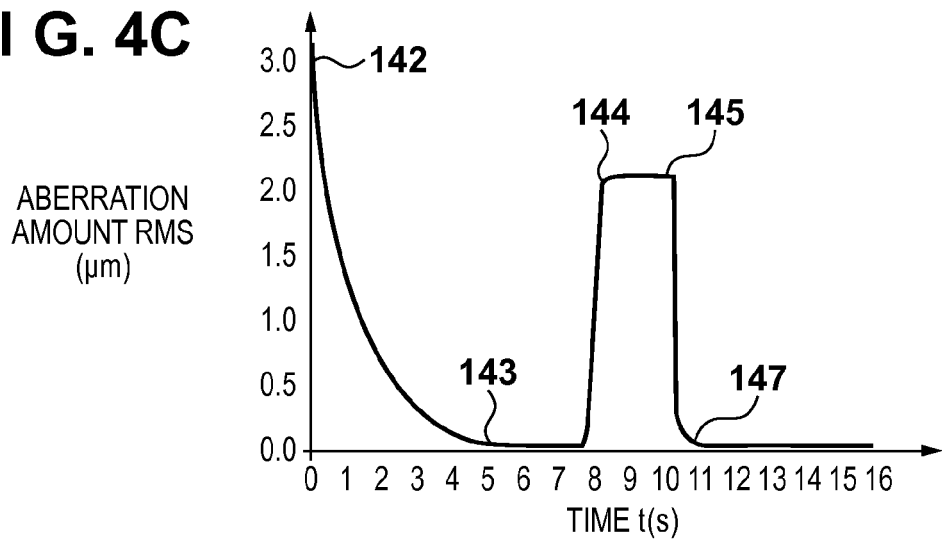

ADAPTIVE OPTICAL APPARATUS, IMAGING APPARATUS, AND CONTROL METHOD AND PROGRAM

BACKGROUND OF THE INVENTION

Field of the Invention

The present invention relates to an adaptive optical apparatus, an imaging apparatus, and a control method and program for the adaptive optical apparatus.

Description of the Related Art

Recently, an imaging apparatus (SLO: Scanning Laser Ophthalmoscope, to be also referred to as an SLO apparatus hereinafter) that two-dimensionally irradiates a fundus with a laser beam and receives the reflected light has been developed as an ophthalmic imaging apparatus. Also, an imaging apparatus has been developed (to be also referred to as an OCT apparatus hereinafter) using optical coherence tomography (OCT) that involves the interference of low-coherence light. In particular, the OCT apparatus is used to acquire a tomographic image of an object to be examined (for example, the fundus or its vicinity of an eye to be examined), because the apparatus can acquire a tomographic image with a resolution equivalent to about the wavelength of light entering an object to be examined.

Various kinds of OCT apparatuses have been developed such as a TD-OCT apparatus (Time Domain OCT) and an SD-OCT apparatus (Spectral Domain OCT). Recently, the resolution of particularly an ophthalmic imaging apparatus like this has been increased by increasing the NA (numerical aperture) of an irradiation laser. When imaging an object to be examined (for example, a fundus), however, the object must be imaged through eye optical tissues such as the cornea and crystalline lens. As the resolution increases, the aberrations of the cornea and crystalline lens exert a large influence on the image quality of an acquired image.

Accordingly, an AO-SLO apparatus (adaptive optics scanning laser ophthalmoscope) and AO-OCT apparatus have been studied that incorporate AO (Adaptive Optics) as an adaptive optical apparatus that measures the aberration of an object to be examined and corrects the aberration. The AO-SLO apparatus or AO-OCT apparatus generally measures the wavefront of an eye by using a wavefront sensor using the Shack-Hartmann wavefront sensor system. In the Shack-Hartmann wavefront sensor system, the wavefront aberration of an object to be examined is measured by irradiating the object with measurement light, and receiving the reflected light by a CCD (charge-coupled device) camera through a microlens array. An aberration correction device (a variable shape mirror or spatial phase modulator) is driven to correct the measured wavefront aberration, and the object to be examined is imaged through the device. Consequently, the AO-SLO apparatus and AO-OCT apparatus can perform high-resolution imaging.

An image acquisition apparatus including a general adaptive optical system performs feedback control that repeats a process of measuring the aberration of an eye and correcting the aberration by using the measurement result. Such a feedback process is beneficial because an error can occur between an instruction value for an aberration correction device and an actual correction amount, and the aberration can fluctuate due to a tear (i.e., water) in an eye or a change in the state of refraction. Aberration correction control is the same as general feedback control in that a predetermined time is necessary before an appropriate aberration correction state is reached after the start of processing. It takes a few seconds to a few tens of seconds before an appropriate correction state is obtained because the response speed of particularly a wavefront sensor or wavefront correction device used for aberration correction is low.

The position of an eye sometimes temporarily changes. In this state, the aberration measurement position in the eye is also changed, so the aberration measurement result is temporarily largely changed. As described above, the aberration is normally kept corrected by feedback control, but the eye's position often immediately returns to the original position. In this case, the aberration measurement result is largely changed again. This further prolongs the time required to reach an appropriate correction state.

Japanese Patent Laid-Open No. 2011-104125 has disclosed an ophthalmic apparatus that interrupts the control of an aberration correction device when it is detected that the eye's position has changed, and resumes the control of the aberration correction device from the interrupted state when the eye's position has returned to the original position.

The aberration measurement result is temporarily largely changed not only because the eye's position is changed, but also because an object that obstructs the measurement of the eye's aberration has entered between the pupil of the eye and the apparatus, for example, a blink of the eye has occurred.

More specifically, when the eyelid is closed by a blink of the eye, the measurement light cannot pass through the eyelid, so the aberration measurement result is temporarily changed to a large extent. As described previously, the aberration is normally kept corrected by feedback control. When an eye blink occurs, however, the eyelid immediately opens, so the aberration measurement result is changed by a large amount again. This further prolongs the time required to reach an appropriate correction state.

This present invention can shorten the time required to reach an appropriate correction state.

SUMMARY OF THE INVENTION

According to one aspect of the present invention, there is provided an adaptive optical apparatus comprising: a correction unit configured to correct a wavefront aberration of an eye to be examined; a detection unit configured to detect that an eyelid of the eye to be examined is closed or the eyelid of the eye to be examined is open, by using return light from the eye to be examined irradiated by measurement light; and a control unit configured to control the correction unit according to a detection result from the detection unit.

In the present invention, when a detector detects that an object that obstructs the measurement of a wavefront aberration has entered between an object to be examined and a measurement unit (for example, when the detector detects that the eyelid of an eye to be examined has closed), a controller interrupts a correction process being performed by a correction unit. When the detector detects that the object that obstructs the measurement of a wavefront aberration has come out from between the object to be examined and the measurement unit (for example, when the detector detects that the eyelid of the eye has opened), the controller can resume correction by the correction unit from the interrupted state. This makes it possible to shorten the time required to reach an appropriate correction state.

Further features of the present invention will become apparent from the following description of exemplary embodiments (with reference to the attached drawings).

BRIEF DESCRIPTION OF THE DRAWINGS

FIG. 2 is a view for explaining a configuration example of an imaging apparatus according to the second embodiment;

FIGS. 3A to 3E-2 are views for explaining an aberration correction device and wavefront sensor of the imaging apparatus according to the first embodiment;

FIGS. 4A to 4C are views for explaining an aberration correcting function of an adaptive optical apparatus of the imaging apparatus according to the first embodiment.

DESCRIPTION OF THE EMBODIMENTS

Embodiments of the present invention will exemplarily be explained in detail below with reference to the accompanying drawings. However, constituent elements described in the embodiments are merely examples, and the technical scope of the present invention is determined by the scope of the appended claims and is not limited by the following individual embodiments.

First Embodiment: Detection of Presence/Absence of Object that Obstructs Aberration Measurement by Output from Wavefront Sensor As an adaptive optical apparatus and imaging apparatus according to the first embodiment of the present invention, a configuration example of an AO-SLO apparatus including an adaptive optical apparatus will be explained below. Note that the present invention is not limited to the AO-SLO apparatus, and is similarly applicable to an AO-OCT apparatus.

Figure 1:
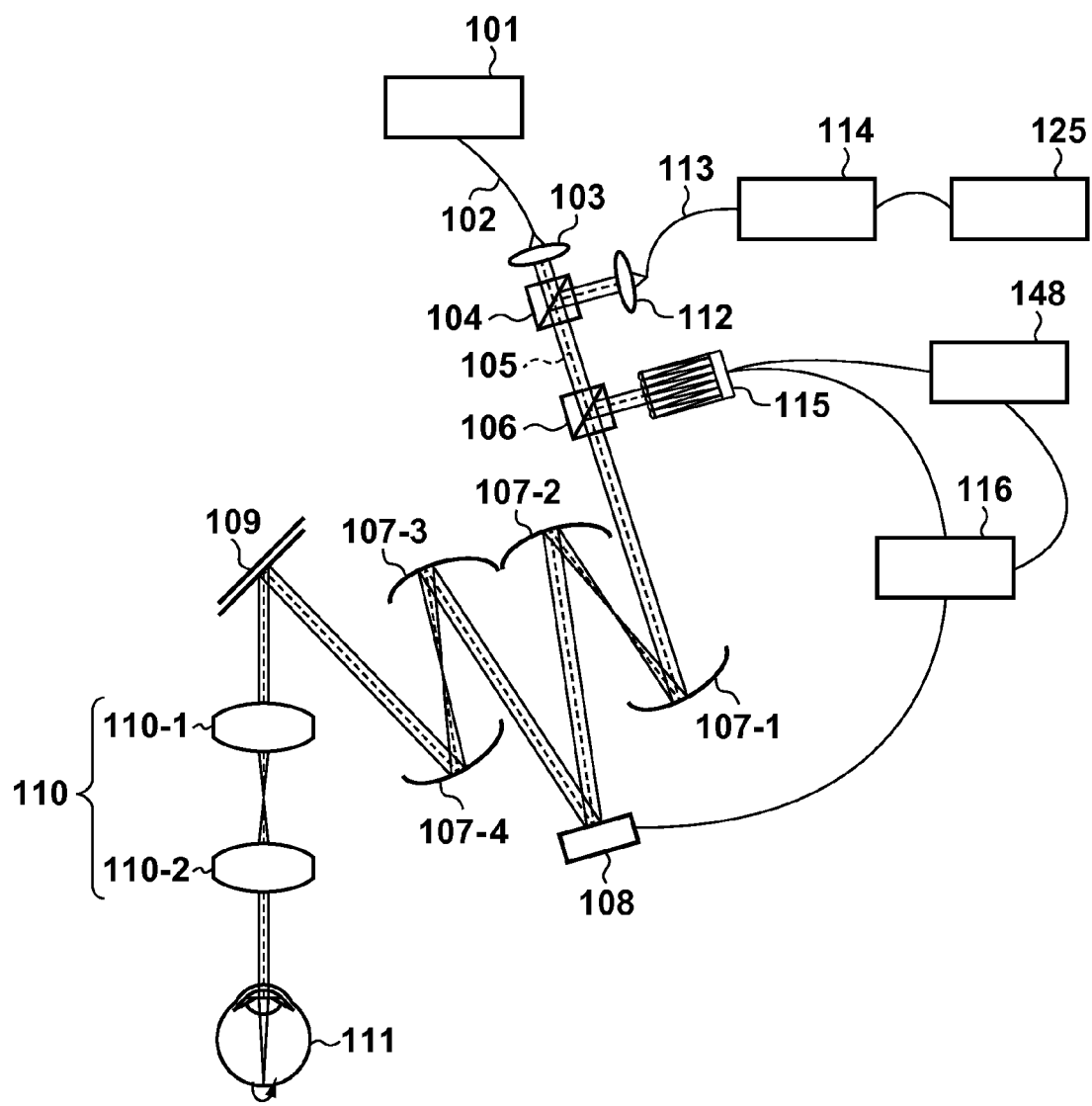
FIG. 1 is a view for explaining a configuration example of an imaging apparatus according to the first embodiment.

Referring to FIG. 1, a light source 101 can be, for example, an SLD (Super Luminescent Diode) light source having a wavelength of 840 nm. Although the wavelength of the light source 101 is not particularly limited, it is possible to apply a light source capable of generating light having a wavelength of, for example, about 800 to 1,500 nm, as a light source for fundus imaging, in order to reduce glare of an object to be examined and maintain the resolution. It is also possible to use a laser or the like, instead of the SLD light source. When using a laser, however, an arrangement for decreasing the interference, for example, an arrangement for passing the laser through an optical fiber at a long distance is added in order to reduce speckle noise. In this embodiment, the same light source is used for both fundus imaging and wavefront measurement. However, it is also possible to use different light sources, and multiplex two light components midway along an optical path.

Light emitted from the light source 101 is passed through a single-mode optical fiber 102, and emitted as a parallel light beam from a collimator 103. Measurement light 105 transmitted through a light splitting unit 104 is guided to an adaptive optical apparatus. As the light splitting unit 104, it is possible to apply, for example, a beam splitter or fiber coupler. The light splitting ratio of the light splitting unit 104 can be set at an optimum ratio in accordance with an object to be examined.

The adaptive optical apparatus includes a light splitting unit 106, a wavefront sensor (aberration measurement unit) 115, an aberration correction device (aberration correction unit) 108, and reflecting mirrors 107-1 to 107-4 for guiding light to these units. Like the light splitting unit 104, a beam splitter, fiber coupler, or the like can be applied as the light splitting unit 106, and the light splitting ratio of the light splitting unit 106 can be set at an optimum ratio in accordance with an object to be examined.

The reflecting mirrors 107 are arranged such that at least an object to be examined (for example, the pupil of an eye to be examined), the wavefront sensor 115, and the aberration correction device 108 have an optically conjugate relationship. As the aberration correction device 108, it is possible to use, for example, a variable shape mirror or spatial phase modulator. FIG. 3A is a view exemplarily showing a variable shape mirror as the aberration correction device 108. This variable shape mirror includes a deformable film-like mirror surface 127 that reflects incident light, a base 126, and actuators 128 sandwiched between them. Examples of the operation principle of the actuators 128 are an electrostatic force, magnetic force, and piezoelectric effect, and the arrangement of the actuators 128 changes in accordance with the operation principle. A plurality of actuators 128 are two-dimensionally arranged on the base 126, and the mirror surface 127 can freely be deformed by selectively driving the actuators 128. The light reflecting direction can locally be changed by this deformation of the mirror surface 127.

As another configuration example of the aberration correction device 108, it is possible to use, for example, a spatial phase modulator (reflection type liquid crystal light modulator) as shown in FIG. 3B. This spatial phase modulator has a structure in which liquid crystal molecules 132-1 and 132-2 are sealed in a space sandwiched between the base 129 and cover 130. The base 129 has a plurality of pixel electrodes 131, and the cover 130 has a transparent counterelectrode (not shown).

When no voltage is applied between the pixel electrode 131 and counterelectrode, the liquid crystal molecules are aligned as indicated by reference numeral 132-1. When a voltage is applied between the electrodes, the aligned state 132-1 of the liquid crystal molecules changes to an aligned state as indicated by reference numeral 132-2, and the refractive index for the incident light changes. Spatial phase modulation can be performed by changing the refractive index of each pixel by controlling the voltage of each pixel electrode. For example, when incident light 133 enters an element, the phase of light passing through the liquid crystal molecules 132-2 lags behind the phase of light passing through the liquid crystal molecules 132-1, thereby forming a wavefront 134. However, a liquid crystal element has a polarizing characteristic, and hence often includes, for example, a polarizing plate for adjusting the polarization of incident light.

The light having passed through the adaptive optical apparatus is one- or two-dimensionally scanned by a scanning optical unit 109 for scanning light on an object to be examined (for example, the pupil of an eye to be examined). For one-dimensional scanning, for example, it is possible to use an LSLO (Line Scanning Laser Ophthalmoscope) that irradiates an object to be examined with a linear laser, and scans this linear laser in one direction (one-dimensionally). Also, for two-dimensional scanning, it is possible to use two galvanometer scanners for main scanning (in the horizontal direction of the fundus), and sub-scanning (in the vertical direction of the fundus) in a direction perpendicular to the main scanning (in the horizontal direction of the fundus). To increase the imaging speed, it is also possible to use a resonance scanner on the main scanning side of the scanning optical system 109.

Depending on the arrangement, it is also possible to use an optical system such as a mirror or lens between the scanners in the scanning optical system 109 in order to set these scanners in an optically conjugate state. The light scanned by the scanning optical unit 109 irradiates an eye 111 to be examined through an eyepiece unit 110 (eyepiece lenses 110-1 and 110-2). The light (measurement light) radiated to the eye 111 to be examined is reflected or scattered by the fundus. By adjusting the positions of the eyepiece lenses 110-1 and 110-2, optimum irradiation can be performed in accordance with the eyesight of the eye 111 to be examined. Although the eyepiece lenses are used as the eyepiece unit 110 in this embodiment, the eyepiece unit 110 may also be formed by using a spherical mirror or the like.

Return light reflected and scattered from the fundus of the eye 111 to be examined propagates through the same path as that of the incident light in the opposite direction. A part of the return light reflected by the light splitting unit 106 (a beam splitter) enters the wavefront sensor 115, and is used to measure the wavefront of the return light.

In this embodiment, a Shack-Hartmann sensor as shown in FIGS. 3C-1 and 3C-2 is used as the wavefront sensor 115. Referring to FIG. 3C-1, light 135 is the return light from the eye 111 to be examined, and irradiates a focal plane 138 on a CCD sensor 137 through a microlens array 136. FIG. 3C-2 is a view showing the section in a position indicated by A-A' in FIG. 3C-1, and shows the way the microlens array 136 is formed by a plurality of microlenses 139. The light 135 is divided into spots equal in number to the microlenses 139 through the microlens array 136, and these spots irradiate the CCD sensor 137. FIG. 3D is a view showing the state in which the CCD sensor 137 is irradiated with the light. The light having passed through the microlens array 136 irradiates the CCD sensor 137 as spots 140.

The wavefront sensor 115 is connected to an adaptive optical controller 116, and transmits the received light (spots 140) as the wavefront of the light 135 to the adaptive optical controller 116. The adaptive optical controller 116 acquires (calculates) the wavefront aberration of the incident light 135 from the positions of the spots 140. FIGS. 3E-1 and 3E-2 are schematic views when a wavefront having a spherical aberration is measured. The light 135 is formed by a wavefront as indicated by reference numeral 141. The light 135 is radiated to a local position in a perpendicular-line direction by the microlens array 136. FIG. 3E-2 shows the irradiated state of the CCD sensor 137 in this case. Since the light 135 has a spherical aberration, the spots 140 are radiated as they are deviated toward to a central portion. The wavefront aberration of the light 135 can be acquired by calculating this position.

A part of the return light transmitted through the light splitting unit 106 (a beam splitter) is reflected by the light splitting unit 104 (a beam splitter), and guided to a light intensity sensor 114 through a collimator 112 and optical fiber 113. The light intensity sensor 114 converts the return light into an electrical signal. An image processor 125 generates a fundus image by using the electrical signal converted by the light intensity sensor 114.

(Detection Unit 148 for Detecting Presence/Absence of Object that Obstructs Aberration Measurement)

From the information of the wavefront sensor 115, a detection unit 148 detects that an object that obstructs aberration measurement has entered between an object to be examined and the wavefront sensor 115, or the object that obstructs aberration measurement has come out from between the object to be examined and the wavefront sensor 115. Examples of the object that obstructs aberration measurement are the eyelid of an eye to be examined, the eyelashes of an eye to be examined, the hair of an object to be examined, and a part of the body of an object to be examined. If the object that obstructs aberration measurement enters between an object to be examined (for example, an eye to be examined) and the wavefront sensor 115, the light amount of return light from the wavefront sensor 115 changes. The detection unit 148 detects the presence/absence of the object that obstructs aberration measurement from the change in light amount of return light from the wavefront sensor 115. The following explanation will be made by taking the eyelid of an eye to be examined as an example of the object that obstructs aberration measurement. The detection unit 148 detects that the eyelid of an eye to be examined has closed by regarding that the object that obstructs aberration measurement has entered between an object to be examined and the wavefront sensor 115. Also, the detection unit 148 detects that the eyelid of the eye to be examined has opened by regarding that the object that obstructs aberration measurement has come out from between the pupil of the eye and the wavefront sensor 115. The adaptive optical controller 116 functions as a controller for performing feedback control on the aberration correcting process performed by the aberration correction device 108, in order to correct an aberration occurring in an eye to be examined. The adaptive optical controller 116 calculates correction information for correcting the aberration from the information of the wavefront sensor 115, and instructs the connected aberration correction device 108. For example, when the aberration correction device 108 is formed by a variable shape mirror, the adaptive optical controller 116 calculates the shape, which cancels the aberration, of the reflection surface of the variable shape mirror, based on the information acquired from the wavefront sensor 115. Then, the adaptive optical controller 116 instructs the aberration correction device 108 (a variable shape mirror) to deform the shape of the reflection surface into the above-mentioned shape.

The process by which the wavefront sensor 115 measures the wavefront and the adaptive optical controller 116 acquires the wavefront aberration and instructs the aberration correction device 108 to deform the shape of the reflection surface is repetitively performed, thereby performing feedback control so as to obtain an optimum wavefront.

Based on the detection result (measurement result) from the detection unit 148, the adaptive optical controller 116 determines interruption of feedback control for the aberration correction device 108.

When the detection unit 148 detects that the eyelid is closed by a blink, the adaptive optical controller 116 temporarily interrupts feedback control. When the detection unit 148 detects that the eyelid has opened after the interruption of correction (when no blink has been detected any longer or, more specifically, when the detection unit 148 detects that the eye is open), the adaptive optical controller 116 resumes feedback control. When detecting that the eyelid is closed by a blink during imaging, the detection unit 148 transmits the detection result to the adaptive optical controller 116. The adaptive optical controller 116 having received this transmission temporarily interrupts feedback control by maintaining the aberration correction state when the closure of the eyelid is detected (before the interruption). When the detection unit 148 detects that the eyelid has opened after the interruption of correction, the adaptive optical controller 116 resumes feedback control from the maintained correction state.

Aberration correction performed by the adaptive optical apparatus will be explained below with reference to FIGS. 4A to 4C. FIG. 4A shows the result of aberration correction performed by a normal aberration correcting function. The ordinate indicates a measured aberration amount (RMS:

Root Mean Square), and the abscissa indicates a time (in seconds) required to correct the aberration by feedback control. When correction is started, an aberration of about 3 µm exists as indicated by reference numeral 142. The adaptive optical controller 116 performs feedback control based on the measured aberration, thereby gradually correcting the aberration. An approximately aplanatic state is reached at around a point indicated by reference numeral 143.

A high-resolution image can be obtained when fundus imaging is performed at this point of time. Since the aberration is thus corrected by feedback control, it takes a few seconds to reduce the aberration to an amount by which high-resolution imaging is possible. Note that while the aberration is being corrected by feedback control, the aberration amount is still large, so a high-resolution image is difficult to obtain.

Next, the fluctuation in aberration in the related art when a blink occurs in an eye to be examined as an object to be examined will be explained with reference to FIG. 4B. When a blink occurs, the eyelid blocks the radiation of measurement light to the eye 111 to be examined, so no reflected and scattered light (no return light) comes from the retina to the wavefront sensor 115. This makes it impossible to detect the number of spots 140, which is necessary to calculate the wavefront, on the CCD sensor 137, and aberration measurement causes a detection error. Consequently, feedback control of aberration correction is performed on an aberration obtained by the detection error.

Referring to FIG. 4B, when aberration correction is started, an initial aberration is corrected as indicated by reference numeral 142 in the same manner as shown in FIG. 4A, then a state indicated by reference numeral 143 is reached. When a blink occurs at time 144 after that, a wrong aberration is detected, so the aberration changes. Then, when the eyelid opens at time 145, reflected and scattered light (return light) comes from the retina to the wavefront sensor 115 again, and an aberration is accurately measured, so the aberration changes again. Before an aplanatic state is obtained by performing feedback control on this aberration, the time further elapses until time 146. Although the blink is complete at time 145, the aberration remains, so no high-resolution image can be obtained at time 146, and further feedback control is necessary.

Figure 5:
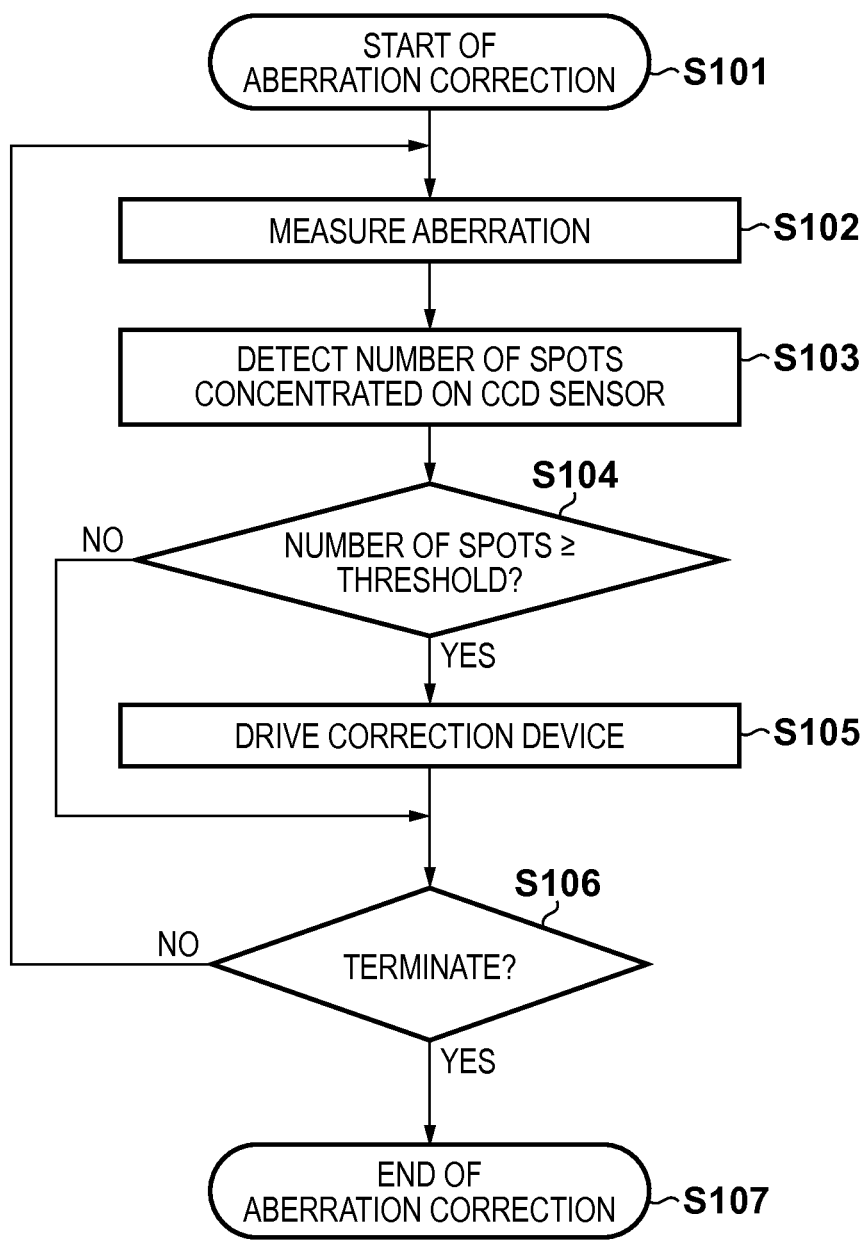
FIG. 5 is a view for explaining the procedure of aberration correction according to the first embodiment.

FIG. 5 is a view for explaining the procedure of aberration correction according to the first embodiment of the present invention. First, aberration correction is started in step S101. In step S102, the wavefront sensor 115 measures an aberration. In step S103, the detection unit 148 detects the number of spots of reflected and scattered light from the retina, which is focused on the CCD sensor 137.

Then, in step S104, the detection unit 148 determines whether the number of spots detected in step S103 is equal to or larger than a preset threshold, and outputs the determination result to the adaptive optical controller 116. If the number of spots is equal to or larger than the threshold, the return light reflected and scattered from the retina has entered the wavefront sensor 115. Therefore, the detection unit 148 determines that the eyelid is not closed by a blink (the eyelid is open). If the number of spots is smaller than the threshold, the detection unit 148 determines that the eyelid is closed by a blink. Note that in this embodiment, whether the eyelid is closed by a blink is detected by comparing the number of spots with the preset threshold. However, it is also possible to record the change in number of spots with time, and determine that the eyelid is closed if the change amount is equal to or larger than a preset threshold. Alternatively, although whether the eyelid is closed is detected based on the number of spots, it is also possible to calculate the light intensity of the reflected and scattered light coming from the retina to the wavefront sensor 115, and detect whether the eyelid is closed in accordance with whether the light intensity is equal to or higher than a preset threshold.

If the number of spots is equal to or larger than the threshold (if the eyelid is not closed (the eyelid is open)) in the determination process in step S104 (Yes in step S104), the process advances to step S105, and the adaptive optical controller 116 drives the aberration correction device 108 based on the aberration information. On the other hand, if the number of spots is smaller than the threshold (if the eyelid is closed) in the determination process in step S104 (No in step S104), the process advances to step S106 by skipping step S105. Under the control of the adaptive optical controller 116, the aberration correction device 108 interrupts aberration correction, and maintains the present correction state.

In step S106, the adaptive optical controller 116 compares the aberration sensed by the wavefront sensor 115 with a threshold aberration as a reference. If the sensed aberration is larger than the threshold aberration, the adaptive optical controller 116 determines to continue the aberration correcting process (No in step S106). Then, the process is returned to step S102. On the other hand, if the sensed aberration is equal to or smaller than the threshold aberration in step S106, the adaptive optical controller 116 determines to terminate the aberration correcting process (Yes in step S106). Then, the process advances to step S107, and aberration correction is terminated (step S107).

FIG. 4C is a view showing the result of aberration correction performed by the above-mentioned procedure. When correction is started, an aberration of about 3 µm exists as indicated by reference numeral 142. The adaptive optical controller 116 performs feedback control based on the measured aberration, thereby gradually correcting the aberration. An approximately aplanatic state is reached at around a point indicated by reference numeral 143.

When the eyelid is closed by a blink at time 144 after that, no return light reflected and scattered by the retina enters the wavefront sensor 115, so it is impossible to detect the number of spots 140, which is necessary to calculate the wavefront, on the CCD sensor 137. At this time, the detection unit 148 detects that the eyelid is closed by a blink, and the adaptive optical controller 116 does not drive the aberration correction device 108 but maintains the present state (interruption of aberration correction). Since the state of the aberration correction device 108 remains unchanged, the aberration amount detected at time 144 remains, but no problem arises because no image is acquired in this state.

When the detection unit 148 detects that the eyelid has opened at time 145 after correction is interrupted, the adaptive optical controller 116 starts (resumes) feedback control for the aberration correction device 108 from the interrupted state. When feedback control is started (resumed), the shape of the reflection surface of the aberration correction device 108 is maintained as a reflection surface shape by which an aberration is approximately zero. After the adaptive optical controller 116 resumes feedback control, therefore, the aberration correction device 108 can correct the aberration at time 145 to an almost aplanatic state within a very short time (from time 145 to time 147). In this case, it is possible to perform acquisition (imaging) of a high-resolution fundus image without any time loss such as that from time 145 to time 146 shown in FIG. 4B.

Second Embodiment: Detection of Presence/Absence of Object that Obstructs Aberration Measurement by Output from Anterior Ocular Segment Observation Camera As an adaptive optical apparatus and imaging apparatus according to the second embodiment of the present invention, a configuration example of an AO-SLO apparatus including an adaptive optical apparatus will be explained below with reference to FIG. 2. The configuration of this AO-SLO apparatus shown in FIG. 2 is basically the same as that of the AO-SLO apparatus explained with reference to FIG. 1, but differs from the configuration of the first embodiment in that a light splitting unit 201 and an anterior ocular segment observation camera 202 for acquiring an image of the anterior ocular segment of an eye to be examined are arranged before an eye 111 to be examined. As the light splitting unit 201, it is possible to use, for example, a beam splitter or perforated mirror.

Note that in this embodiment, whenever each frame of a moving image of the anterior ocular segment is acquired by the anterior ocular segment observation camera 202, it is favorable to store the measurement result from a wavefront sensor 115 in association with the frame. This is because if a detection unit 148 detects that an object that obstructs the measurement of a wavefront aberration comes out from between an object to be examined and the wavefront sensor 115, correction by an aberration correction device 108 can be resumed by using the measurement result from the wavefront sensor 115 which has detected that the object comes out when a frame corresponding to the above-mentioned detection is acquired. This can make the resumption timing of wavefront aberration correction earlier. Note that in the first embodiment, the above-mentioned detection is performed by using the measurement result from the wavefront sensor 115. Therefore, it is unnecessary to store the frame and measurement result in association with each other as described above, and correction by the aberration correction device 108 need only be resumed by using the measurement result from the wavefront sensor 115, which is temporally immediately before the frame of interest. This can make the resumption timing of wavefront aberration correction earlier as in this embodiment.

The anterior ocular segment observation camera 202 acquires an image (moving image) of the anterior ocular segment of the eye 111 to be examined through the light splitting unit 201 (a beam splitter) at a predetermined time interval. Consequently, a moving image having a predetermined frame rate (the reciprocal of the time interval) is obtained. The anterior ocular segment observation camera 202 transmits each frame of this moving image to the detection unit 148 in real time. Note that the anterior ocular segment observation camera 202 can also transmit frames thinned at a predetermined time interval to the detection unit 148, instead of transmitting all frames of the moving image to the detection unit 148.

Also, light emitted from a light source 101 is emitted as a parallel light beam by a collimator 103. As in the first embodiment, measurement light 105 transmitted through a light splitting unit 104 irradiates the eye 111 to be examined through the adaptive optical apparatus and an eyepiece unit 110. Return light reflected and scattered by the retina of the eye 111 to be examined propagates through the same path as that of the incident light in the opposite direction. A part of the return light reflected by a light splitting unit 106 enters the wavefront sensor 115, and is used to measure the wavefront of the return light.

A part of the return light transmitted through the light splitting unit 106 is reflected by the light splitting unit 104, and guided to a light intensity sensor 114 through a collimator 112 and optical fiber 113. The light intensity sensor 114 converts the return light into an electrical signal. An image processor 125 generates a fundus image by using the electrical signal converted by the light intensity sensor 114.

The wavefront sensor 115 is connected to an adaptive optical controller 116, and transmits the received light (spots 140) as the wavefront of light 135 to the adaptive optical controller 116. The adaptive optical controller 116 acquires the wavefront aberration of the incident light 135 from the positions of the spots 140. Then, the adaptive optical controller 116 calculates correction information for correcting the aberration from the information of the wavefront sensor 115, and instructs the connected aberration correction device 108. For example, the adaptive optical controller 116 calculates the shape of the reflection surface of a variable shape mirror, which corrects the aberration to obtain an aplanatic wavefront, based on the information acquired from the wavefront sensor 115. Then, the adaptive optical controller 116 instructs the aberration correction device 108 (a variable shape mirror) to deform the shape of the reflection surface into the above-mentioned shape. The process by which the wavefront sensor 115 measures the wavefront and the adaptive optical controller 116 acquires the wavefront aberration and instructs the aberration correction device 108 to deform the shape of the reflection surface is performed repeatedly, thereby performing feedback control so as to obtain an optimum wavefront.

In this embodiment, the detection unit 148 detects that the eyelid is closed by a blink of the eye 111 to be examined, by using the image of the anterior ocular segment acquired by the anterior ocular segment observation camera 202. The detection unit 148 specifies, from each frame, an image region (pupil image region) corresponding to the pupil of the eye 111 to be examined. This process is to specify an approximately circular low-luminance image region in a frame. Note that while the eye 111 to be examined is not moving, the image region (pupil image region) exists near the center of a frame.

If the image region (pupil image region) is specified, the detection unit 148 determines that the eyelid is not closed by a blink when the frame is acquired. On the other hand, if no image region (pupil image region) is specified, the detection unit 148 determines that the eyelid is closed by a blink when the frame is acquired.

This determination process by the detection unit 148 corresponds to the process in step S104 of FIG. 5 explained in the first embodiment. In this embodiment, the operation from the acquisition of each frame by the anterior ocular segment observation camera 202 to the determination process is executed in real time without intervening the adaptive optical apparatus. Therefore, whether the eyelid is closed by a blink of the eye to be examined can be determined without any time lag. As in the first embodiment, if the eyelid is not closed (if the eyelid is open) (Yes in step S104), the process advances to step S105, and the adaptive optical controller 116 drives the aberration correction device 108 based on the aberration information. On the other hand, if the eyelid is closed (No in step S104), the process is advanced to step S106 by skipping step S105, and the aberration correction device 108 maintains the present state (interruption of aberration correction).

Then, when the detection unit 148 detects that the eyelid is open (the blink is complete), the adaptive optical controller 116 starts (resumes) feedback control for the aberration correction device 108 from the state in which feedback control is interrupted. When feedback control is started (resumed), the shape of the reflection surface of the aberration correction device 108 is maintained as a reflection surface shape by which an aberration is approximately zero as indicated by time 143 shown in FIG. 4C. After the adaptive optical controller 116 resumes feedback control, therefore, the aberration correction device 108 can correct the aberration at time 145 to an almost aplanatic state within a very short time (from time 145 to time 147). In the arrangement of this embodiment in which the operation from the acquisition of each frame to the determination process is executed in real time, it is possible to rapidly perform the acquisition (imaging) of a high-resolution fundus image without any time loss such as that from time 145 to time 146 in FIG. 4B.

In this embodiment, whether the eyelid is closed by a blink is detected by using a moving image of the anterior ocular segment. However, the present invention is not limited to this. For example, whether the eyelid is closed by a blink may also be detected by projecting a light spot onto the cornea or retina of the eye 111 to be examined, and imaging the cornea or fundus onto which the light spot is projected by using the anterior ocular segment observation camera 202. If the light spot is specified, the detection unit 148 can determine that the eyelid is not closed (the eyelid is open). If no light spot is specified, the detection unit 148 can determine that the eyelid is closed. It is possible to rapidly perform the acquisition (imaging) of a high-resolution fundus image without any time loss even when using the projection result of the light spot.

Third Embodiment: Application of Adaptive Optical Apparatus of First Embodiment to Imaging of Fundus Image In the first and second embodiments, feedback control of aberration correction performed when it is detected that the eyelid is closed by a blink has been explained. In this embodiment, a case in which the first embodiment is applied to practical imaging of a fundus image of an eye to be examined will be explained. To perform imaging of a fundus image, measurement light 105 from a light source 101 irradiates the fundus of an eye 111 to be examined via an adaptive optical apparatus and eyepiece unit 110, and return light reflected and scattered by the fundus returns to a wavefront sensor 115 by propagating through the same path as that of the incident light in the opposite direction. A detection unit 148 counts the number of spots on a CCD sensor 137 of the wavefront sensor 115. The number of spots is basically determined by the beam diameter of the measurement light and the pitch of the lens array. However, the number of spots is counted during measurement because it is affected by an eye to be examined as an object to be examined. After this counting by the detection unit 148, an adaptive optical controller 116 performs feedback control of aberration correction as explained in the first embodiment. In this control, a threshold indicating that the eyelid is closed by a blink is set at 90% of the number of spots when the eyelid is not closed (when the eyelid is open). For example, assuming that the number of spots is 1,000 when the eyelid is not closed (when the eyelid is open), the detection unit 148 determines that the eyelid is closed by a blink if the number of counted spots is smaller than 900. If the number of counted spots is 900 or more, the detection unit 148 determines that the eyelid is not closed (the eyelid is open).

In parallel with this feedback control of aberration correction, an image processor 125 generates fundus images based on outputs from a light intensity sensor 114, and sequentially stores the generated images in a storage unit (memory) (not shown). In this embodiment, when the image processor 125 stores the fundus images in the memory, the detection result from the detection unit 148 is associated with each fundus image as identification information indicating whether the eyelid is closed, and stored in the storage unit (memory). For example, when an image generated by the image processor 125 is an image acquired when the eyelid is closed, information indicating that the image is acquired while a blink occurs (during the occurrence of a blink) is added to the fundus image and stored in the storage unit (memory). Also, when a generated image is an image acquired when the eyelid is not closed (when the eyelid is open), information indicating that there is no blink is added to the fundus image and stored in the storage unit (memory). Furthermore, information indicating the possibility of the start of a blink is added to a fundus image (for example, an image of one or two frames) immediately before the closure of the eyelid is detected, and stored in the memory.

When displaying a series of fundus images on a display unit (not shown), the display unit can perform display control based on the identification information indicating whether the eyelid is closed. For example, the display unit can read out and display images acquired when the eyelid is open by excluding images acquired when the eyelid is closed. It is also possible to display the identification information indicating whether the eyelid is closed, together with the fundus image.

In each of the above embodiments, when the detection unit 148 detects that an object that obstructs aberration measurement has entered between an object to be examined and the wavefront sensor 115 (for example, when the detection unit 148 detects that the eyelid of an eye has closed), the adaptive optical controller 116 interrupts correction by the aberration correction device 108. When the detection unit 148 detects that the object that obstructs aberration measurement comes out from between the object to be examined and wavefront sensor 115 (for example, when the detection unit 148 detects that the eyelid of the eye has opened), the adaptive optical controller 116 can resume correction by the aberration correction unit 108 from the interrupted state. This can shorten the time required to reach an appropriate correction state.

Also, in each of the above embodiments, it is possible to perform aberration correction that reduces the influence of aberration fluctuations caused by a blink, and acquire a high-quality image within a short time by reducing the influence of aberration fluctuations caused by a blink.

Furthermore, the adaptive optical apparatus explained in each of the above-described embodiments is applicable not only to an ophthalmic imaging apparatus but also to an endoscope apparatus. In this case, the endoscope apparatus need only include a light source, the adaptive optical apparatus, and an insertion unit that inserts the adaptive optical apparatus into a body (body cavity). Examples of an object that obstructs aberration measurement in this case are a masticatory substance of ingested food and a secretion such as saliva. When an object that obstructs aberration measurement enters between an object to be examined and the wavefront sensor 115, the light amount of return light on the wavefront sensor 115 changes. The detection unit 148 detects the presence/absence of the object that obstructs aberration measurement from the change in light amount of the return light on the wavefront sensor 115.

When the detection unit 148 detects that the object that obstructs aberration measurement has entered between the object to be examined and wavefront sensor 115, the adaptive optical controller 116 interrupts correction by the aberration correction device 108. When the detection unit 148 detects that the object that obstructs aberration measurement has come out from between the object to be examined and wavefront sensor 115, the adaptive optical controller 116 resumes correction by the aberration correction device 108 from the interrupted state. This can shorten the time required to reach an appropriate correction state.

Note that it is preferable to measure, by using a measuring means such as a timer, an elapsed time since the detection unit 148 detects that an object that obstructs aberration measurement has entered between an object to be examined and the wavefront sensor. If the elapsed time exceeds a predetermined time, it is favorable to interrupt correction by the aberration correction device 108, and prevent the measurement light from irradiating the object to be examined by, for example, closing a shutter (not shown). As a consequence, if the object that obstructs aberration measurement has entered between the object to be examined and wavefront sensor for a long time period, it is possible to determine that aberration correction is impossible, and prevent unnecessary measurement light from irradiating the object to be examined.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-261633, filed Nov. 29, 2012, which is hereby incorporated by reference herein in its entirety.

What is claimed is:

1. An adaptive optical apparatus comprising:
an irradiation unit configured to irradiate an eye with measurement light;
a wavefront aberration measurement unit configured to measure a wavefront aberration of the eye and to measure a number of spots obtained by using return light from the eye irradiated with the measurement light;
a wavefront aberration correction unit configured to correct the wavefront aberration of the eye;
a detection unit configured to detect whether the number of spots which is measured by the wavefront aberration measurement unit is less than a threshold; and
a control unit configured to control the wavefront aberration correction unit according to a measurement result of the wavefront aberration measurement unit and a detection result of the detection unit.

2. The apparatus according to claim 1, wherein the detection unit is operable to detect, in a case where the number of spots which is measured by the wavefront aberration measurement unit is less than a threshold, that an eyelid of the eye is closed, and to detect, in a case where the number of spots which is measured by the wavefront aberration measurement unit is not less than the threshold, that the eyelid of the eye is open,
wherein the control unit is operable to control, in a case where the detection unit detects that the eyelid of the eye has gone from an open state to a closed state, the wavefront aberration correction unit to interrupt correction, and
wherein the control unit is operable to control, in a case where the detection unit detects that the eyelid of the eye has reopened, the wavefront aberration correction unit to resume the interrupted correction.

3. The apparatus according to claim 2, wherein the control unit controls the wavefront aberration correction unit according to a detection result of the detection unit to determine a correction state,
wherein in a case where the correction has been interrupted, the wavefront aberration correction unit is configured to maintain the correction state of the wavefront aberration when it is detected that the eyelid of the eye is closed, and
wherein in a case where the interrupted correction is resumed, the wavefront aberration correction unit is configured to resume correction from the maintained correction state.

4. The apparatus according to claim 1, further comprising an acquisition unit configured to acquire an image of an anterior ocular segment of the eye by using the return light,
wherein the detection unit is operable to detect, in a case where the number of spots which is measured by the wavefront aberration measurement unit is less than a threshold, that an eyelid of the eye is closed, and to detect, in a case where the number of spots which is measured by the wavefront aberration measurement unit is not less than the threshold, that the eyelid of the eye is open,
wherein in a case where an image region corresponding to a pupil of the eye cannot be specified in the image, the detection unit is configured to detect that the eyelid of the eye is closed, and
wherein in a case where the image region can be specified, the detection unit is configured to detect that the eyelid of the eye is open.

5. The apparatus according to claim 4, wherein the acquisition unit is operable to acquire a moving image of the anterior ocular segment of the eye at a predetermined frame rate,
wherein in a case where the image region cannot be specified in a frame of the moving image, the detection unit is configured to detect that the eyelid of the eye is closed, and
wherein in a case where the image region can be specified in a frame, the detection unit is configured to detect that the eyelid of the eye is open.

6. An imaging apparatus including:
an adaptive optical apparatus; and
a generation unit configured to generate an image of the eye of which the wavefront aberration is corrected by the adaptive optical apparatus,
wherein the adaptive optical apparatus comprises:
(1) an irradiation unit configured to irradiate an eye with measurement light;
(2) a wavefront aberration measurement unit configured to measure a wavefront aberration of the eye and to measure a number of spots obtained by using return light from the eye irradiated with the measurement light;
(3) a wavefront aberration correction unit configured to correct the wavefront aberration of the eye;
(4) a detection unit configured to detect, in a case where the number of spots which is measured by the wavefront aberration measurement unit is less than a threshold, that an eyelid of the eye is closed and to detect, in a case where the number of spots which is measured by the wavefront aberration measurement unit is not less than the threshold, that the eyelid of the eye is open; and
(5) a control unit configured to control the wavefront aberration correction unit according to a measurement result of the wavefront aberration measurement unit and a detection result of the detection unit.

7. A control method of an adaptive optical apparatus, the method comprising:
(1) an irradiation step of irradiating an eye with measurement light;
(2) a wavefront aberration measurement step of measuring a wavefront aberration of the eye and of measuring a number of spots obtained by using return light from the eye irradiated with the measurement light;
(3) a wavefront aberration correction step of correcting, by a wavefront aberration correction unit, the wavefront aberration of the eye;
(4) a detection step of detecting whether the number of spots which is measured in the wavefront aberration measurement step is less than a threshold; and
(5) a control step of controlling the wavefront aberration correction unit according to a measurement result of the wavefront aberration measurement step and a detection result of the detection step.

8. The method according to claim 7, wherein in a case where the number of spots which is measured in the wavefront aberration measurement step is less than a threshold, it is detected that an eyelid of the eye is closed, and in a case where the number of spots which is measured in the wavefront aberration measurement step is not less than the threshold, it is detected that the eyelid of the eye is open,
wherein in a case where it is detected that the eyelid of the eye has gone from an open state to a closed state, the wavefront aberration correction unit is controlled to interrupt correction, and
wherein in a case where it is detected that the eyelid of the eye has reopened, the wavefront aberration correction unit is controlled to resume the interrupted correction.

9. An imaging apparatus control method comprising:
a control process of an adaptive optical apparatus, the control process including (1) an irradiation step of irradiating an eye with measurement light, (2) a wavefront aberration measurement step of measuring a wavefront aberration of the eye and of measuring a number of spots obtained by using return light from the eye irradiated with the measurement light, (3) a wavefront aberration correction step of correcting, by a wavefront aberration correction unit, the wavefront aberration of the eye, (4) a detection step of detecting, in a case where the number of spots which is measured in the wavefront aberration measurement step is less than a threshold, that an eyelid of the eye is closed, and of detecting, in a case where the number of spots which is measured in the wavefront aberration measurement step is not less than the threshold, that the eyelid of the eye is open, and (5) a control step of controlling the wavefront aberration correction unit according to a measurement result of the wavefront aberration measurement step and a detection result of the detection step; and
a generation step of generating an image of the eye of which the wavefront aberration is corrected by the adaptive optical apparatus.

10. A non-transitory computer-readable storage medium storing a program for causing a computer to execute a control method of an adaptive optical apparatus, the method comprising:
(1) an irradiation step of irradiating an eye with measurement light;
(2) a wavefront aberration measurement step of measuring a wavefront aberration of the eye and of measuring a number of spots obtained by using return light from the eye irradiated with the measurement light;
(3) a wavefront aberration correction step of correcting, by a wavefront aberration correction unit, the wavefront aberration of the eye;
(4) a detection step of detecting whether the number of spots which is measured in the wavefront aberration measurement step is less than a threshold; and
(5) a control step of controlling the wavefront aberration correction unit according to a measurement result of the wavefront aberration measurement step and a detection result of the detection step.

11. The apparatus according to claim 6, wherein the control unit is configured to control, in a case where the detection unit detects that the eyelid of the eye has gone from an open state to a closed state, the wavefront aberration correction unit to interrupt correction, and to control, in a case where the detection unit detects that the eyelid of the eye has reopened, the wavefront aberration correction unit to resume the interrupted correction.

12. The apparatus according to claim 1, wherein the detection unit is operable to detect, in a case where the number of spots which is measured by the wavefront aberration measurement unit is less than a threshold, that an eyelid of the eye is closed, and to detect, in a case where the number of spots which is measured by the wavefront aberration measurement unit is not less than the threshold, that the eyelid of the eye is open,
wherein the apparatus further comprises a count unit configured to count an elapsed time since the detection unit detects that the eyelid of the eye is closed, and
wherein the control unit controls, in a case where the elapsed time exceeds a predetermined time, the wavefront aberration correction unit to interrupt correction.

13. The method according to claim 9, wherein in a case where it is detected in the detection step that the eyelid of the eye has gone from an open state to a closed state, the wavefront aberration correction unit is controlled to interrupt correction, and in a case where it is detected in the detection step that the eyelid of the eye has reopened, the wavefront aberration correction unit is controlled to resume the interrupted correction.

14. A non-transitory computer-readable storage medium storing a program for causing a computer to execute an imaging apparatus control method, the method comprising:
    a control process of an adaptive optical apparatus, the control process including (1) an irradiation step of irradiating an eye with measurement light, (2) a wavefront aberration measurement step of measuring a wavefront aberration of the eye and of measuring a number of spots obtained by using return light from the eye irradiated with the measurement light, (3) a wavefront aberration correction step of correcting, by a wavefront aberration correction unit, the wavefront aberration of the eye, (4) a detection step of detecting, in a case where the number of spots which is measured in the wavefront aberration measurement step is less than a threshold, that an eyelid of the eye is closed, and detecting, in a case where the number of spots which is measured in the wavefront aberration measurement step is not less than the threshold, that the eyelid of the eye is open, and (5) a control step of controlling the wavefront aberration correction unit according to a measurement result of the wavefront aberration measurement step and a detection result of the detection step; and
    a generation step of generating an image of the eye of which the wavefront aberration is corrected by the adaptive optical apparatus.

15. The apparatus according to claim 1, further comprising a display unit,
    wherein the control unit causes, in a case where the number of spots which is measured by the wavefront aberration measurement unit is less than the threshold, the display unit to display identification information indicating that the eyelid of the eye is closed, and
    wherein the control unit causes, in a case where the number of spots which is measured by the wavefront aberration measurement unit is not less than the threshold, the display unit to display identification information indicating that the eyelid of the eye is open.

16. The method according to claim 7, further comprising a display control step of causing, in a case where the number of spots which is measured in the wavefront aberration measurement step is less than the threshold, a display unit to display identification information indicating that the eyelid of the eye is closed, and causing, in a case where the number of spots which is measured in the wavefront aberration measurement step is not less than the threshold, the display unit to display identification information indicating that the eyelid of the eye is open.

17. The apparatus according to claim 6, further comprising a storage unit,
    wherein in a case where the number of spots which is measured by the wavefront aberration measurement unit is less than the threshold, the control unit stores, in the storage unit, the generated image and identification information indicating that the eyelid of the eye is closed, and
    wherein in a case where the number of spots which is measured by the wavefront aberration measurement unit is not less than the threshold, the control unit stores, in the storage unit, the generated image and identification information indicating that the eyelid of the eye is open.

18. The method according to claim 9, further comprising a storage step of storing, in a storage unit, the generated image and identification information indicating that the eyelid of the eye is closed, in a case where the number of spots which is measured in the wavefront aberration measurement step is less than the threshold, and storing, in the storage unit, the generated image and identification information indicating that the eyelid of the eye is open, in a case where the number of spots which is measured in the wavefront aberration measurement step is not less than the threshold.

19. The apparatus according to claim 17, further comprising a display unit,
    wherein the control unit reads out an image stored in the storage unit together with identification information indicating that the eyelid of the eye is open, and causes the display unit to display the read out image.

20. The method according to claim 18, further comprising a display control step of reading out an image stored in the storage unit together with identification information indicating that the eyelid of the eye is open, and causing a display unit to display the read out image.

21. The apparatus according to claim 1, wherein the control unit is operable to control, in a case where the detection unit detects that the number of spots which is measured by the wavefront aberration measurement unit is less than the threshold, the wavefront aberration correction unit to interrupt correction, and
    wherein, after correction has been interrupted, the control unit is operable to control, in a case where the detection unit then detects that the number of spots which is measured by the wavefront aberration measurement unit is not less than the threshold, the wavefront aberration correction unit to resume the interrupted correction.

22. The method according to claim 7, wherein in a case where it is detected that the number of spots which is measured in the wavefront aberration measurement step is less than the threshold, the wavefront aberration correction unit is controlled to interrupt correction, and
    wherein, after correction has been interrupted, in a case where it is then detected that the number of spots which is measured in the wavefront aberration measurement step is not less than the threshold, the wavefront aberration correction unit is controlled to resume the interrupted correction.

* * * * *